United States Patent
Shah et al.

(10) Patent No.: US 9,072,476 B2
(45) Date of Patent: Jul. 7, 2015

(54) FLEXIBLE SENSOR APPARATUS

(75) Inventors: Rajiv Shah, Rancho Palos Verdes, CA (US); Rebecca K. Gottlieb, Culver City, CA (US); Eric A. Larson, Moorpark, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 2068 days.

(21) Appl. No.: 11/234,722

(22) Filed: Sep. 23, 2005

(65) Prior Publication Data

US 2007/0073129 A1    Mar. 29, 2007

(51) Int. Cl.
| A61B 5/05 | (2006.01) |
| A61B 5/00 | (2006.01) |
| A61B 5/1486 | (2006.01) |
| A61B 5/145 | (2006.01) |
| A61B 17/34 | (2006.01) |

(52) U.S. Cl.
CPC ......... *A61B 5/14865* (2013.01); *A61B 5/14532* (2013.01); *A61B 5/6849* (2013.01); *A61B 2017/3407* (2013.01); *A61B 2562/164* (2013.01)

(58) Field of Classification Search
CPC ........... A61B 5/14532; A61B 5/14865; A61B 5/14546; A61B 5/1486; A61B 5/6833; A61B 5/6848
USPC ......................................... 600/345, 347, 365
See application file for complete search history.

(56) References Cited

U.S. PATENT DOCUMENTS

| 4,433,072 A | 2/1984 | Pusineri et al. |
| 4,494,950 A | 1/1985 | Fischell |
| 4,557,723 A * | 12/1985 | Sibalis ............................ 604/20 |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |

(Continued)

FOREIGN PATENT DOCUMENTS

| EP | 0 281 421 A2 | 9/1988 |
| EP | 0 678 308 A1 | 10/1994 |

(Continued)

OTHER PUBLICATIONS

Abel et al., "Experience with an implantable glucose sensor as a prerequisite of an artificial beta cell," Biomed. Biochim. Acta, 1984, pp. 577-584, vol. 5.

(Continued)

*Primary Examiner* — Michael D'Angelo
*Assistant Examiner* — Christian Jang
(74) *Attorney, Agent, or Firm* — Pillsbury Winthrop Shaw Pittman LLP

(57) ABSTRACT

A flexible mounting base to hold a sensor at an infusion site, the sensor being a removable in vivo sensor for monitoring analyte concentration level in a patient, such as blood glucose (BG) level. The mounting base comprises a flexible adhesive that anchors the flexible sensor set at an infusion site to provide stability for the sensor set in a convenient and comfortable manner. Placement of the mounting base onto the patient's skin causes the insertion needle to pierce the skin for transcutaneous placement of the cannula with the sensor therein. The insertion needle can then be withdrawn to leave the cannula and sensor at the selected insertion position, with the distal segment of the sensor being exposed to patient extracellular fluid via apertures formed in the cannula.

38 Claims, 8 Drawing Sheets

(56) References Cited

U.S. PATENT DOCUMENTS

| | | | |
|---|---|---|---|
| 4,731,726 | A | 3/1988 | Allen, III |
| 4,762,516 | A | 8/1988 | Luther et al. |
| 4,781,798 | A | 11/1988 | Gough |
| 4,871,351 | A | 10/1989 | Feingold |
| 5,080,653 | A | 1/1992 | Voss et al. |
| 5,097,122 | A | 3/1992 | Colman et al. |
| 5,101,814 | A | 4/1992 | Palti |
| 5,108,819 | A | 4/1992 | Heller et al. |
| 5,165,407 | A | 11/1992 | Wilson et al. |
| 5,262,035 | A | 11/1993 | Gregg et al. |
| 5,262,305 | A | 11/1993 | Heller et al. |
| 5,264,104 | A | 11/1993 | Gregg et al. |
| 5,264,105 | A | 11/1993 | Gregg et al. |
| 5,284,140 | A | 2/1994 | Allen et al. |
| 5,299,571 | A | 4/1994 | Mastrototaro |
| 5,320,725 | A | 6/1994 | Gregg et al. |
| 5,322,063 | A | 6/1994 | Allen et al. |
| 5,356,786 | A | 10/1994 | Heller et al. |
| 5,370,622 | A | 12/1994 | Livingston et al. |
| 5,371,687 | A | 12/1994 | Holmes, II et al. |
| 5,376,070 | A | 12/1994 | Purvis et al. |
| 5,390,671 | A | 2/1995 | Lord et al. |
| 5,391,250 | A * | 2/1995 | Cheney et al. ............... 156/268 |
| 5,403,700 | A | 4/1995 | Heller et al. |
| 5,411,647 | A | 5/1995 | Johnson et al. |
| 5,482,473 | A | 1/1996 | Lord et al. |
| 5,497,772 | A | 3/1996 | Schulman et al. |
| 5,543,326 | A | 8/1996 | Heller et al. |
| 5,569,186 | A | 10/1996 | Lord et al. |
| 5,586,553 | A | 12/1996 | Halili et al. |
| 5,593,852 | A | 1/1997 | Heller et al. |
| 5,660,163 | A | 8/1997 | Schulman et al. |
| 5,665,065 | A | 9/1997 | Colman et al. |
| 5,665,222 | A | 9/1997 | Heller et al. |
| 5,750,926 | A | 5/1998 | Schulman et al. |
| 5,779,665 | A | 7/1998 | Mastrototaro et al. |
| 5,791,344 | A | 8/1998 | Schulman et al. |
| 5,904,708 | A | 5/1999 | Goedeke |
| 5,917,346 | A | 6/1999 | Gord et al. |
| 5,965,380 | A | 10/1999 | Heller et al. |
| 5,972,199 | A | 10/1999 | Heller et al. |
| 5,999,848 | A | 12/1999 | Gord et al. |
| 5,999,849 | A | 12/1999 | Gord et al. |
| 6,043,437 | A | 3/2000 | Schulman et al. |
| 6,081,736 | A | 6/2000 | Colvin et al. |
| 6,083,710 | A | 7/2000 | Heller et al. |
| 6,088,608 | A | 7/2000 | Schulman et al. |
| 6,103,033 | A | 8/2000 | Say et al. |
| 6,119,028 | A | 9/2000 | Schulman et al. |
| 6,120,676 | A | 9/2000 | Heller et al. |
| 6,121,009 | A | 9/2000 | Heller et al. |
| 6,134,461 | A | 10/2000 | Say et al. |
| 6,143,164 | A | 11/2000 | Heller et al. |
| 6,162,611 | A | 12/2000 | Heller et al. |
| 6,175,752 | B1 | 1/2001 | Say et al. |
| 6,259,937 | B1 | 7/2001 | Schulman et al. |
| 6,329,161 | B1 | 12/2001 | Heller et al. |
| 6,472,122 | B1 | 10/2002 | Schulman et al. |
| 6,484,046 | B1 | 11/2002 | Say et al. |
| 6,503,381 | B1 | 1/2003 | Gotoh et al. |
| 6,514,718 | B2 | 2/2003 | Heller et al. |
| 6,554,798 | B1 | 4/2003 | Mann et al. |
| 6,558,320 | B1 | 5/2003 | Causey, III et al. |
| 6,560,471 | B1 | 5/2003 | Heller et al. |
| 6,565,509 | B1 | 5/2003 | Say et al. |
| 6,579,690 | B1 | 6/2003 | Bonnecaze et al. |
| 6,591,125 | B1 | 7/2003 | Buse et al. |
| 6,592,745 | B1 | 7/2003 | Feldman et al. |
| 6,605,200 | B1 | 8/2003 | Mao et al. |
| 6,605,201 | B1 | 8/2003 | Mao et al. |
| 6,607,658 | B1 | 8/2003 | Heller et al. |
| 6,616,819 | B1 | 9/2003 | Liamos et al. |
| 6,618,934 | B1 | 9/2003 | Feldman et al. |
| 6,623,501 | B2 | 9/2003 | Heller et al. |
| 6,654,625 | B1 | 11/2003 | Say et al. |
| 6,671,554 | B2 | 12/2003 | Gibson et al. |
| 6,676,816 | B2 | 1/2004 | Mao et al. |
| 6,689,265 | B2 | 2/2004 | Heller et al. |
| 6,733,471 | B1 | 5/2004 | Ericson et al. |
| 6,745,061 | B1 | 6/2004 | Hicks et al. |
| 6,746,582 | B2 | 6/2004 | Heller et al. |
| 6,749,740 | B2 | 6/2004 | Liamos et al. |
| 6,809,653 | B1 | 10/2004 | Mann et al. |
| 6,881,551 | B2 | 4/2005 | Heller et al. |
| 6,893,545 | B2 | 5/2005 | Gotoh et al. |
| 6,916,159 | B2 | 7/2005 | Rush et al. |
| 6,932,894 | B2 | 8/2005 | Mao et al. |
| 6,942,518 | B2 | 9/2005 | Liamos et al. |
| 7,003,336 | B2 * | 2/2006 | Holker et al. ............... 600/316 |
| 2002/0004640 | A1 * | 1/2002 | Conn et al. ............... 604/20 |
| 2002/0082665 | A1 | 6/2002 | Haller et al. |
| 2002/0161288 | A1 | 10/2002 | Shin et al. |
| 2002/0180605 | A1 | 12/2002 | Ozguz et al. |
| 2003/0078560 | A1 | 4/2003 | Miller et al. |
| 2003/0088166 | A1 | 5/2003 | Say et al. |
| 2003/0130616 | A1 * | 7/2003 | Steil et al. ............... 604/66 |
| 2003/0152823 | A1 | 8/2003 | Heller et al. |
| 2003/0168338 | A1 | 9/2003 | Gao et al. |
| 2003/0176183 | A1 | 9/2003 | Drucker et al. |
| 2003/0187338 | A1 * | 10/2003 | Say et al. ............... 600/345 |
| 2003/0188427 | A1 | 10/2003 | Say et al. |
| 2003/0199744 | A1 | 10/2003 | Buse et al. |
| 2003/0220552 | A1 | 11/2003 | Reghabi et al. |
| 2004/0061232 | A1 | 4/2004 | Shah et al. |
| 2004/0061234 | A1 | 4/2004 | Shah et al. |
| 2004/0064133 | A1 | 4/2004 | Miller et al. |
| 2004/0064156 | A1 | 4/2004 | Shah et al. |
| 2004/0074785 | A1 | 4/2004 | Holker et al. |
| 2004/0093167 | A1 | 5/2004 | Braig et al. |
| 2004/0111017 | A1 | 6/2004 | Say et al. |
| 2005/0214585 | A1 | 9/2005 | Li et al. |
| 2006/0016700 | A1 * | 1/2006 | Brister et al. ............... 205/777.5 |

FOREIGN PATENT DOCUMENTS

| EP | 1338295 | 8/2003 |
|---|---|---|
| JP | S63-229062 | 9/1988 |
| WO | WO 96/37246 A1 | 11/1996 |
| WO | WO 00/45696 | 8/2000 |
| WO | WO 02/058537 A2 | 8/2002 |
| WO | WO 2006/017358 A1 | 2/2006 |

OTHER PUBLICATIONS

Reach et al., "A Method for Evaluating in vivo the Functional Characteristics of Glucose Sensors," Biosensors, 1986, pp. 211-220, vol. 2.

Boguslavsky et al., "Applications of redox polymers in biosensors," Solid State Ionics, 1993, pp. 189-197, vol. 60.

Geise et al., "Electropolymerized 1,3-diaminobenzene for the construction of a 1-1'-dimethylferrocene mediated glucose biosensor,"Analytica Chim. Acta., 1993, pp. 467-473, v18.

Gernet et al., "A planar glucose enzyme electrode," Sensors and Actuators, 1989, pp. 537-540, vol. 17, Elsevier Sequoia, Netherlands.

Gernet et al., "Fabrication and Characterization of a Planar Electrochemical Cell and Its Applications as a Glucose Sensor," Sensors and Actuators, 1989, pp. 49-70, vol. 18.

Gorton et al., "Amperometric glucose senosrs based on immobilized glucose-oxidizing enzymes and chemically modified electrodes," Analytica Chim Acta., 1991, pp. 43-54, v. 249.

Gorton et al., "Amperometric biosensors based on an apparent direct electron transfer between electrodes and immobilized peroxidases," Analyst, 1992, pp. 1235-1241, vol. 117.

Gough et al., "Two-Dimensional Enzyme Electrode Sensor for Glucose," Analytical Chemistry, 1985, pp. 2351-2357, vol. 57.

Gregg et al., "Redox polymer films containing enzymes," J. Phys. Chem., 1991, pp. 5970-5975.

Gregg et al., "Cross-Linked Redox Gels Containing Glucose Oxidase for Amperometric Biosensor Applications," Anal. Chem., 1990, pp. 258-263, vol. 62.

Heller et al., "Electrical Wiring of Redox Enzymes," Accounts of Chemical Research, 1990, pp. 128-134, vol. 23, No. 5.

(56) References Cited

OTHER PUBLICATIONS

Johnson et al., "In vivo evaluation of an electroenzymatic glucose sensor implanted in subcutaneous tissue," Biosensors & Bioelectronics, 1992, pp. 709-714, vol. 7.
Jonsson et al., "An Electrochemical Sensor for Hydrogen Peroxide Based on Peroxidase Adsorbed on a Spectrographic Graphite Electrode," Electroanalysts, 1989, pp. 465-468, v.1.
Kanapieniene et al., "Miniature glucose biosensor with extended linearity," Sensors and Actuators, 1992, pp. 37-40, vol. B, No. 10.
Kawamori et al., "Perfect Normalization of Excessive Glucagon Responses to Intravenous Arginine in Human Diabetes Mellitus With . . . ," Diabetes, 1980, pp. 762-765, vol. 29.
Kimura et al., "An immobilized Enzyme Membrane Fabrication Method using an Ink Jet Nozzle," Biosensors, 1988, pp. 41-52, vol. 4.
Koudelka et al., "In-vivio Behaviour of Hypodermically Implanted Microfabricated Glucose Sensors," Biosensors & Bioelectronics, 1991, pp. 31-36, vol. 6.
Mastrototaro et al., "An electroenzymatic glucose sensor fabricated on a flexible substrate," Sensors and Actuators, 1991, pp. 139-144, vol. 5.
Mastrototaro et al., "An Electroenzymatic Sensor Capable of 72 Hour Continuous Monitoring of Subcutaneous Glucose," 14th Int'l Diabetes Federation Congress, 1991.
McKean et al., "A Telemetry-Instrumentation System for Chronically Implanted Glucose and Oxygen Sensors," IEEE Transactions on Biomedical Eng., 1988, pp. 526-532, vol. 35, No. 7.
Monroe, "Novel implantable glucose sensors," ACL, 1989, pp. 8-16.
Morff et al., "Microfabrication of Reproducible, Economical, Electroenzymatic Glucose Sensors," Annual Int'l Conf. IEEE Eng. in Med. and Bio. Soc., 1990, pp. 483-484, v.12, n.2.
Nakamado et al., "A Lift-Off Method for Patterning Enzyme-Immobilized Membranes in Multi-Biosensors," Sensors and Actuators, 1988, pp. 165-172, vol. 13.
Nishida et al., "Clinical applications of the wearable artificial endocrine pancreas with the newly designed . . . ," Path. and Treat. of NIDDM . . . , 1994, p. 353-358, No. 1057.
Shichiri et al., "An artificial endocrine pancrease—problems awaiting solutions for long term clinical applications of . . . ," Frontiers Med. Biol. Eng., 1991, pp. 283-292, v.3.
Shichiri et al., "Wearable Artificial Endocrine Pancreas with Needle-Type Glucose Sensor," The Lancet, 1982, pp. 1129-1131, vol. 2 (8308).
Shichiri et al., "Telemetry Glucose Monitoring Device with Needle-Type Glucose Sensor," Diabetes Care, May-Jun. 1986, pp. 298-301, vol. 9, No. 3.
Shichiri et al., "Normalization of the Paradoxic Secretion of Glucagen in Diabetics Who Were Controlled by the Artificial Beta Cell," Diabetes, 1979, pp. 272-275, vol. 28.
Shichiri et al., "Closed-Loop Glycemic Control with a Wearable Artificial Endocrine Pancreas," Diabetes, 1984, pp. 1200-1202, vol. 33.
Shichiri et al., "In Vivo Characteristics of Needle-Type Glucose Sensor," Hormone and Metabolic Research, 1988, pp. 17-20, vol. 20.
Shichiri et al., "A Needle-Type Glucose Sensor," Life Support Systems: The Journal of the European Society for Artificial Organs, 1984, pp. 7-9, vol. 2, supplement 1.
Shichiri et al., "The Wearable Artificial Endocrine Pancreas with a Needle-Type Glucose Sensor," Acta Pediatr, Jpn, 1984, pp. 358-370, vol. 26.
Shichiri et al., "Glycaemic Control in Pancreatectomized Dogs with a Wearable Artificial Endocrine Pancreas," Diabetologica, 1983, pp. 179-184, vol. 24.
Shichiri et al., "Membrane design for extending the long-life of an implantable glucose sensor," Diab. Nutr. Metab., 1989, pp. 309-313, vol. 2.
Shinkai et al., "Molecular Recognition of Mono- and Di-Saccharides by Phenylboronic Acids in Solvent Extraction and as a Monolayer," J. Chem. Soc., 1991, pp. 1039-1041.
Tamiya et al., "Micro Glucose Sensors Using Electron Mediators Immobilized on a Polypyrrole-Modified Electrode," Sensors and Actuators, 1989, pp. 297-307, v.18.
Tsukagoshi et al., "Specific Complexation with Mono- and Disaccharides That can be Detected by Circular Dichroism," J. Org. Chem., 1991, pp. 4089-4091, vol. 56.
Urban et al., "Minaturized multi-enzyme biosensors integrated with pH sensors on flexible polymer carriers . . . ," Biosensors & Bioelectronics, 1992, pp. 733-739, vol. 7.
Urban et al., "Miniaturized thin-film biosensors using covalently immobilized glucose oxidase," Biosensors & Bioelectronics, 1991, pp. 555-562, vol. 6.
Velho et al., "In vivo calibration of a subcutaneous glucose sensor for determination of subcutaneous glucose kinetics," Diab. Nutr. Metab., 1988 pp. 227-233, v.3.
Yokoyama et al., "Integrated Biosensor for Glucose and Galactose," Analytica Chimica Acta., 1989, pp. 137-142, vol. 218.
Nishida et al., "Development of a ferrocene-mediated needle-type glucose sensor . . . ," Medical Process Through Technology, 1995, pp. 91-103, vol. 21.
Koudelka et al., "Planar Amperometric Enzyme-Based Glucose Microelectrode," Sensors and Actuators, 1989, pp. 157-165, vol. 18.
Yamasaki et al., "Direct measurement of whole blood glucose by a needle-type sensor," Clinica Chemica Acta., 1989, pp. 93-98, vol. 93.
Sternberg et al., "Study and Development of Multilayer Needle-type Enzyme-based Glucose Microsensors," Biosensors, 1988, pp. 27-40, vol. 4.
Shaw et al., "In vitro testing of a simply constructed, highly stable glucose sensor suitable for implantation . . . ," Biosensors & Bioelectronics, 1991, pp. 401-406, vol. 6.
Poitout et al., "A glucose monitoring system for on line estimation in man of blood glucose concentration using a miniaturized . . . ," Diabetologia, 1993, pp. 658-663, vol. 36.
Hashigushi et al., "Development of a Miniaturized Glucose Monitoring System by Combining a Needle-Type Glucose Sensor . . . ," Diabetes Care, 1994, pp. 387-389, v.17, n. 5.
Jobst et al., "Thin-Film Microbiosensors for Glucose-Lactate Monitoring," Anal. Chem., 1996, p. 3173-3179, vol. 68.
Shults et al., "A Telemetry-Instrumentation System for Monitoring Multiple Subcutaneously Implanted Glucose Sensors," IEEE Trans. on Biomed. Eng., 1994, pp. 937-942, v41, n. 10.
Wang et al., "Needle-Type Dual Microsensor for the Simultaneous Monitoring of Glucose and Insulin," Anal. Chem., 2001, pp. 844-847, vol. 73.
Moussey et al., "Performance of Subcutaneously Implanted Needle-Type Glucose Sensors Employing a Novel Trilayer Coating," Anal. Chem., 1993, 2072-2077, vol. 65.
Bindra et al., "Design and in Vitro Studies of a Needle-Type Glucose Sensor for Subcutaneous Monitoring," Anal. Chem., 1991, pp. 1692-1696, vol. 63.
PCT: International Search Report, 4 pgs. (mailed: Aug. 31, 2007).

\* cited by examiner

FLEXIBLE SENSOR APPARATUS

FIELD OF THE INVENTION

1. Field of the Invention

This invention relates generally to devices and methods for placing a sensor at a selected site within the body of a patient. More specifically, this invention relates to a flexible mounting base for a sensor adapted for convenient and comfortable transcutaneous positioning of the sensor electrodes to obtain analyte readings, for example, blood glucose (BG) readings.

2. Description of Related Art

Sensors are generally known in the art for use in a variety of specialized sensor applications. For example, thin film electrochemical sensors have been used to test analyte levels in patients. Such thin film sensors generally comprise one or more thin conductors applied by photolithography mask and etch techniques between thin layers of a nonconductive film material, such as polyimide film. The conductors are shaped to define distal segment ends having an appropriate electrode material thereon, in combination with proximal end contact pads adapted for conductive connection with appropriate electronic monitoring equipment. In recent years, thin film sensors of this general type have been proposed for use as a transcutaneous sensor in medical applications. As one example, thin film sensors have been designed for use in obtaining an indication of BG levels and monitoring BG levels in a diabetic patient, with the distal segment portion of the electrodes positioned subcutaneously in direct contact with patient extracellular fluid. Such readings can be especially useful in adjusting a treatment regimen which typically includes regular administration of insulin to the patient. In this regard, BG readings are particularly useful in conjunction with semi-automated medication infusion pumps of the external type, as generally described in U.S. Pat. Nos. 4,562,751; 4,678,408; and 4,685,903; or automated implantable medication infusion pumps, as generally described in U.S. Pat. No. 4,573,994.

Relatively small and flexible electrochemical sensors have been developed for subcutaneous placement of sensor electrodes in direct contact with patient extracellular fluid, wherein such sensors can be used to obtain periodic readings over an extended period of time. Such thin film sensors hold significant promise in patient monitoring applications, but unfortunately have been difficult to place transcutaneously with the sensor electrodes in direct contact with patient extracellular fluid.

Many of these glucose sensors generally utilize complex structures to mount and hold the sensor set in place on the patient's skin. Some of these structures may themselves cause discomfort due to bulk, excessive rigidity, or the manner of attachment. Moreover, because these sensor systems utilize a component that is positioned transcutaneously, it is very important that the infusion site be stable. Improved thin film sensors and related insertion sets are described in commonly assigned U.S. Pat. Nos. 5,390,671; 5,391,250; 5,482,473; 5,568,806; and 5,586,553 and International Publication No. WO 2004/036183, which are incorporated by reference herein. See also U.S. Pat. No. 5,299,571.

BRIEF SUMMARY OF THE INVENTION

The present invention relates to an improved sensor mounting base adapted to provide quick and easy transcutaneous placement of the film sensor on a patient comfortably and with sufficient stability with which to hold the sensor electrodes in direct contact with patient extracellular fluid.

In accordance with embodiments of the invention, a flexible mounting base for a sensor is provided for measuring an analyte, such as blood glucose, of a patient. The flexible mounting base may be used with different types of sensors, including a flexible analyte sensor. The sensor set is placed at a selected site on the patient's body and stabilized by the flexible mounting base and an adhesive layer that holds the sensor at the infusion site in a comfortable but stable manner. A number of enzyme sensors (e.g., glucose sensors that use the enzyme glucose oxidase to effect a reaction of glucose and oxygen) are known in the art. See, for example, U.S. Pat. Nos. 5,165,407, 4,890,620, 5,390,671 and 5,391,250, and International Publication No. WO 2004/036183, which are herein incorporated by reference. Sensors for monitoring glucose concentration of diabetics are further described in Schichiri, et al., "In Vivo Characteristics of Needle-Type Glucose Sensor-Measurements of Subcutaneous Glucose Concentrations in Human Volunteers," Horm. Metab. Res., Suppl. Ser. 20:17-20 (1988); Bruckel, et al., "In Vivo Measurement of Subcutaneous Glucose Concentrations with an Enzymatic Glucose Sensor and a Wick Method," Klin. Wochenschr. 67:491-495 (1989); and Pickup, et al., "In Vivo Molecular Sensing in Diabetes Mellitus: An Implantable Glucose Sensor with direct Electron Transfer," Diabetologia 32:213-217 (1989), which are herein incorporated by reference. Other sensors are described, for example, in Reach, et al., ADVANCES IN IMPLANTABLE DEVICES, A. Turner (ed.), JAI Press, London, Chap. 1, (1993), which is herein incorporated by reference. See also, commonly assigned U.S. Pat. Application entitled "Sensor with Layered Electrodes," Ser. No. 11/234,523, filed on Sep. 23, 2005, which is herein incorporated by reference.

In certain embodiments, the mounting base is made out of a flexible and breathable material. For example, the mounting base may comprise cloth, band-aid-like material, and the like. Such materials may allow the patient more comfort. The adhesive layer may make it easy to affix or remove the sensor. Re-using the same mounting base would lead to health risks, especially if not sterilized properly. The adhesive of the present invention helps avoid these sanitary risks by allowing the patient to simply replace each adhesive as necessary.

In a certain embodiments, the mounting base comprises several layers and is smaller than the size of a penny. In one embodiment, the entire mounting base is about the thickness of a penny with a diameter that is about half that of a penny. In this embodiment, the mounting base of the sensor has an outer flexible layer, a sealing layer, a semi-rigid housing, and a flexible adhesive layer. The semi-rigid portion helps to substantially stabilize the entire base, specifically around the needle insertion area. In one embodiment, the semi-rigid portion may have the flexibility and rigidity of a guitar pick. Stabilizing the needle insertion area may help to ensure safe, stable entry and exit for needle at infusion site.

In further embodiments, the mounting base is configured to be in a slim configuration so that it can fit closer against the patient's body when worn. The slim shape provides more comfort while being less conspicuous, for example, when worn under clothes.

In certain embodiments, a subcutaneous insertion set is provided with the flexible mounting base for placing the sensor at a selected site within the body of a patient. The insertion set comprises the sensor and further comprises a slotted insertion needle extending through the flexible mounting base adapted for seated mounting onto the patient's skin. The sensor includes a proximal segment carried by the flexible mounting base, and a distal segment protruding from the flexible mounting base and having one or more sensor electrodes thereon. The distal segment of the sensor may be carried within a protective cannula which extends from the flexible mounting base with a portion of the cannula being slidably received within the insertion needle. In other embodiments, the flexible sensor functions without the use of a cannula.

When the flexible mounting base is pressed onto the patient's skin, the insertion needle pierces the skin to transcutaneously place the cannula with the sensor distal segment therein. The insertion needle can be withdrawn from the flexible mounting base, leaving the cannula and sensor distal segment within the patient, to directly contact the patient fluid at the selected position within the patient, such as a subcutaneous, intravascular, intramuscular, or intravenous site. Conductive contacts on the sensor proximal segment end can be electrically connected to a suitable monitor device, either by wired or wireless communication, so that appropriate blood chemistry readings can be taken.

During insertion, the insertion needle and the protective cannula cooperatively protect and guide the sensor to the desired transcutaneous placement position. The insertion needle can then be withdrawn, whereupon the slotted needle geometry permits the insertion needle to slide over and longitudinally separate from the second portion of the cannula, thereby leaving the cannula and sensor therein at the selected infusion site.

In further embodiments, a flexible cable is attached to the flexible sensor through a passage into the mounting base. The flexible cable allows communication between the distal sensor tip at a selected in vivo sensor site and the appropriate monitor. The flexible cable may also allow communication between the sensor and an implanted control unit which signals the infusion pump to deliver medication to the patient.

In particular embodiments, a connector fitting is included to provide a convenient and relatively simple structure for anchoring the flexible cable in electrical coupled relation with a telemetry unit, such as a monitor. In such embodiments, the connector fitting may be positioned on the flexible cable, some distance away from the sensor site, rather than being positioned directly on the sensor set. In embodiments where the connector fitting is located away from the sensor set, the flexible cable is easily accessed for periodic removal and replacement of the monitor, without requiring removal or replacement of other system components. Additionally, because the connector fitting is located away from the sensor set, the attached monitor may be stored away from the infusion site. In this configuration, the potential aggravation of the infusion site or contamination of the monitor from the infusion site is minimized.

Optional peripheral devices may include a remote station, such as a bedside monitor. In a hospital setting, one monitor may be used to oversee the BG readings of several patients at once through links to their BG sensor. Other devices that can function as a remote station for monitoring and programming include, but are not limited to, a computer, a hospital database, a cellular telephone, a PDA, a smart phone or internet.

In another embodiment, there may be a needle protection guard included. In this embodiment, when the insertion needle is withdrawn, a protective sheath contained in the flexible mounting base is dislodged and covers the needle tip as the needle is separated from the flexible mounting base. In an alternative, the flexible mounting base may be used with a needle that has a needle guide shaft covering a portion of the needle.

Other features and advantages of the present invention will become more apparent from the following detailed description, taken in conjunction with the accompanying drawings which illustrate, by way of example, the principles of the invention.

BRIEF DESCRIPTION OF THE DRAWINGS

A detailed description of embodiments of the invention will be made with reference to the accompanying drawings, wherein like numerals designate corresponding parts in the figures.

DETAILED DESCRIPTION OF THE INVENTION

In the following description, reference is made to the accompanying drawings which form a part hereof and which illustrate several embodiments of the present inventions. It is understood that other embodiments may be utilized and structural and operational changes may be made without departing from the scope of the present inventions.

In accordance with embodiments of the invention, a flexible mounting base for a sensor is provided for measuring an analyte, such as blood glucose, of a patient. The flexible mounting base may be used with different types of sensors, including a flexible analyte sensor. The sensor set is placed at a selected site on the patient's body and stabilized by the flexible mounting base and a flexible adhesive layer that holds the sensor at the infusion site in a comfortable but stable manner.

Figure 1A:
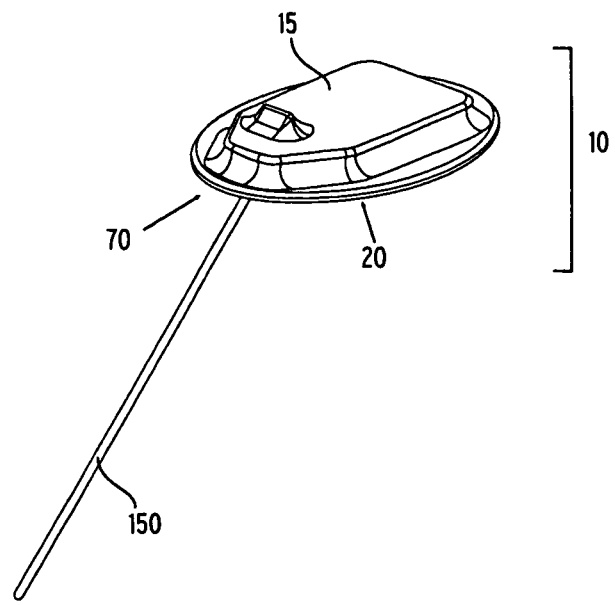
FIG. 1a is a perspective view illustrating a flexible mounting base according to an embodiment of the invention.
Figure 1B:
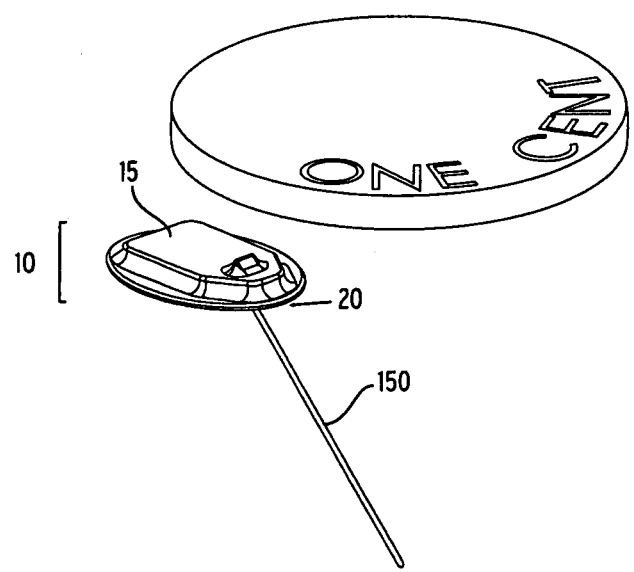
FIG. 1b is a comparison view illustrating the size of a flexible mounting base compared to a penny according to an embodiment of the invention.

In one preferred embodiment, as shown in FIGS. 1a and 1b, the flexible mounting base 10 has a relatively flat shape and is smaller than a penny. In one embodiment, the entire mounting base is about the thickness of a penny with a diameter that is about half that of a penny. The mounting base 10 includes an adhesive layer 20 and carries a flexible sensor 70. The adhesive layer 20 is positioned as a bottom layer of the mounting base 10. An outer layer 15 is flexible and is positioned as a top layer of the mounting base 10. The flexible mounting base 10 is configured to be in a slim configuration so that it can fit closer against the patient's body when worn. The slim shape provides comfort while being relatively inconspicuous, for example, when worn under clothes. For example, the adhesive layer 20 may have a thickness from about 0.015 inches to about 0.025 inches. In embodiments, the adhesive layer 20 is of an oval shape with a length of about 0.26 inches and a width of about 0.38 inches. In some embodiments, the entire mounting base 10 with the flexible sensor 70 is approximately 0.06 inches thick, including the adhesive layer 20, not to exceed past 0.1 inches. The outer layer 15 is flexible and can include materials such as cloth, band-aid-like material, nylon, and like. Generally, any thin polymer material may be used for the outer layer 15. Such materials may allow the patient more comfort. The adhesive layer 20 may make it easy to affix or remove the sensor. The flexible mounting base 10 of the present invention comprises inexpensive materials and is disposable.

Figure 2:
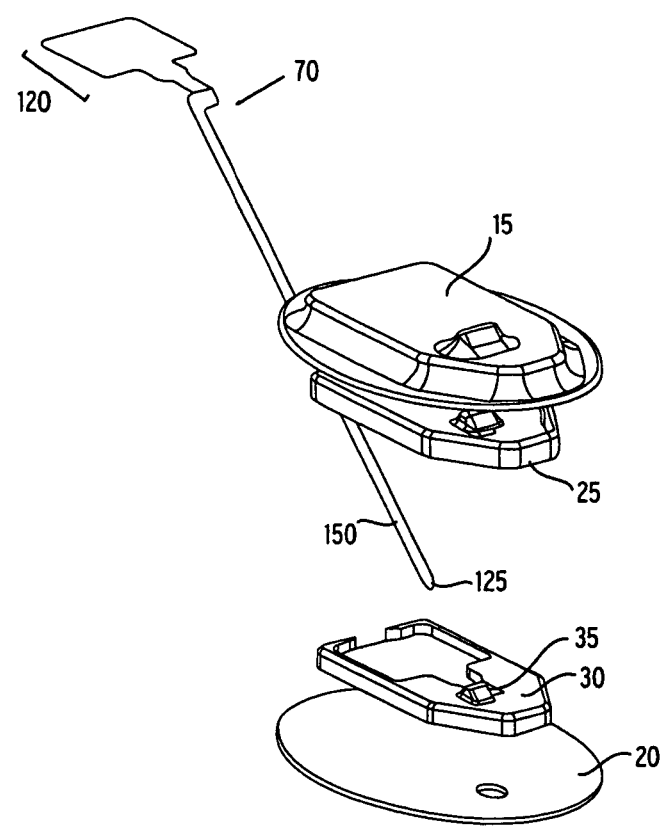
FIG. 2 is an exploded view of a flexible mounting base with a sensor according to an embodiment of the invention.

In FIG. 2, the mounting base 10 is more clearly shown as comprising several layers. These layers include an outer flexible layer 15, a sealing layer 25, a semi-rigid housing 30, and an adhesive layer 20. The semi-rigid housing 30 helps substantially stabilize the entire base, specifically around the areas that the needle enters and exits. A sensor 70 is shown as extending from the mounting base 10. The sensor 70 includes a proximal segment 120 and a distal segment 125. The proximal segment 120 is generally adapted for conductive connection with appropriate electronic monitoring equipment, while the distal segment 125 includes the electrodes positioned subcutaneously in direct contact with the extracellular fluid of a patient. An extension lead 150 connects the proximal segment 120 to the distal segment 125.

Figure 3A:
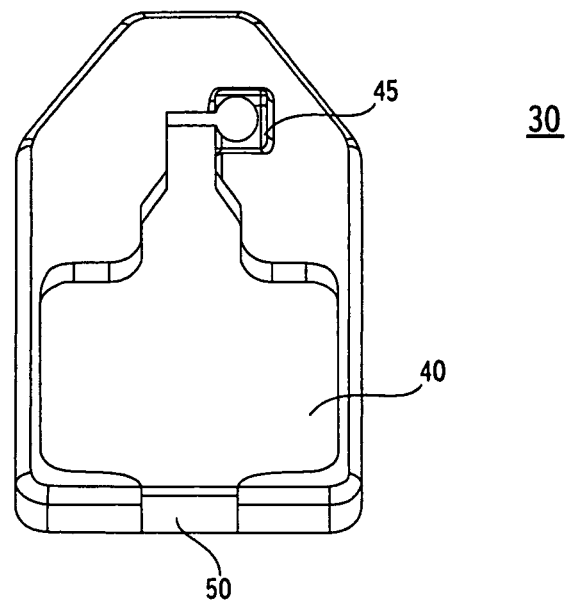
FIG. 3a is an enlarged top view of a semi-rigid housing according to an embodiment of the invention.

FIG. 3a illustrates the semi-rigid housing 30 in more detail. The semi-rigid housing 30 comprises materials that have an amount of both flexibility and rigidity, such as for example, medical grade nylon. The flexibility and rigidity of the housing may be similar to that of a guitar pick. The semi-rigid housing 30 provides for an area, such as a depression, that can hold or receive a sensor and any flexible cables attached to the sensor. The area is known as a flex interface 40. The flex interface 40 is illustrated as a three-walled depression with an opening at one end. The opening may be an exit 50 in the semi-rigid housing 30 to provide an passage for a cable, as well as the extension lead, to pass through. The flexible cable allows communication between the distal sensor tip at a selected in vivo sensor site and the appropriate monitor. The flexible cable may be attached to the flexible sensor through the passage into the mounting base. In an embodiment, the opening or exit 50 is located at a base level of the semi-rigid housing 30 and allows the cable to travel between the adhesive layers. The flexible cable may also allow communication between the sensor and an implanted control unit which signals the infusion pump to deliver medication to the patient. The semi-rigid housing 30 may further include another opening 45 which provides for needle entry. In the shown embodiment, the opening 45 for needle entry is located in one end of the semi-rigid housing 30 and the exit 50 is located on an opposing end of the semi-rigid housing 30. In other embodiments, the positions may vary.

In particular embodiments, a connector fitting is included to provide a convenient and relatively simple structure for anchoring the flexible cable in electrically coupled relation with a telemetry unit, such as a monitor. In such embodiments, the connector fitting may be positioned on the flexible cable, some distance away from the sensor site, rather than being positioned directly on the sensor set. In embodiments where the connector fitting is located away from the sensor set, the flexible cable is easily accessed for periodic removal and replacement of the monitor, without requiring removal or replacement of other system components. Additionally, because the connector fitting is located away from the sensor set, the attached monitor may be stored away from the infusion site. In this configuration, the potential aggravation of the infusion site or contamination of the monitor from the infusion site is minimized.

The sensor 70 carried by the flexible mounting base 10 may further be in communication with a remote station, such as a bedside monitor (not shown). Communication with such optional peripheral devices may be through a data transfer system, using wireless communication such as radio frequency (RF), infrared (IR), WiFi, ZigBee, Bluetooth or other wireless methods. In a hospital setting, a single monitor may be used to oversee the BG readings of several patients at once through links to their BG sensor. Other devices that can function as a remote station for monitoring and programming include, but are not limited to, a computer, a cellular telephone, a PDA, or a smart phone.

Figure 3B:
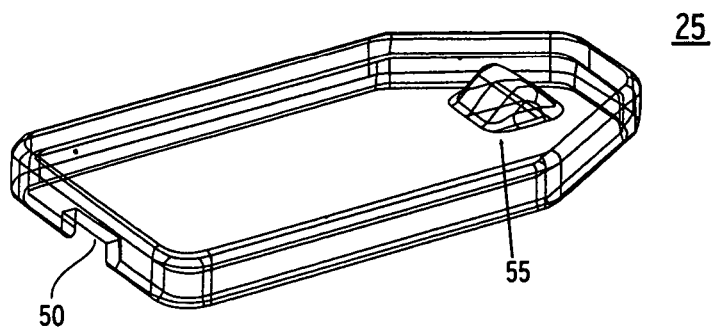
FIG. 3b is an enlarged perspective view of a sealing layer according to an embodiment of the invention.

FIG. 3b illustrates the sealing layer 25 in more detail. The sealing layer 25 may comprise an expandable substance that expands to re-fill any punctures in the layer. For example, the sealing layer 25 may comprise of silicone or a latex material. Other materials may include medical grade polyurethane or synthetic rubbers such as neoprene, nitrile, butyl, and vitron. In the illustrated embodiment, the needle punctures the sealing layer 25 at an area for the needle to enter, or a penetration area 55, to reach the infusion site. When the needle is removed, the silicone will collapse back and re-fill the puncture, creating a seal. The sealing layer 25 provides a more sanitary infusion site by keeping the infusion site insulated. The sealing layer 25 does not need to be fully extended to form an entire layer of the mounting base. In alternative embodiments, not shown, the expandable substance may be located so that it is only covering the needle insertion area. In addition, the sealing layer may be created immediately before inserting the needle, for example, the needle insertion area can be filled with expandable substance prior to the insertion. The sealing layer 25 also includes an opening or an exit 50 to provide an passage for the cable to pass through. In the shown embodiment, the exit 50 is located in one end of the sealing layer 25 and the penetration area 55 is located on an opposing end of the sealing layer 25. In other embodiments, the positions may vary.

Figure 3C:
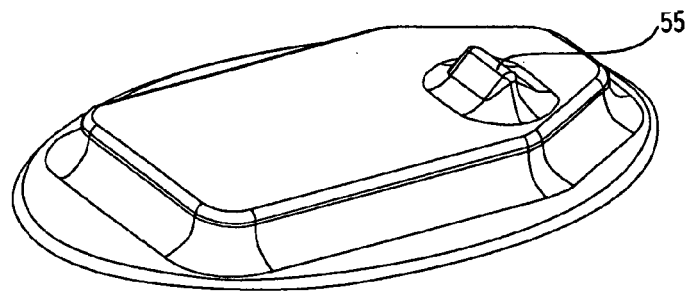
FIG. 3c is an enlarged perspective view of an outer flexible layer according to an embodiment of the invention.

FIG. 3c illustrates the outer flexible layer 15 in more detail. The outer flexible layer 15 may comprise materials such as cloth, band-aid-like material, and the like. For example, materials could include polyurethane, polyethylene, polyester, polypropylene, PTFE, or other polymers. These could be woven, knitted, non-woven, molded, or extruded, for example. Additionally, the material may be flesh-colored to provide more discreteness. A penetration area 55 for needle entry is located on the outer flexible layer 15 and is the initial entry of the needle to the infusion site. The penetration area 55 may also form a needle guide in some embodiments. As with the sealing layer, the needle simply penetrates the outer flexible layer 15 at the penetration area 55 to access the other layers and the infusion site.

Figure 3D:
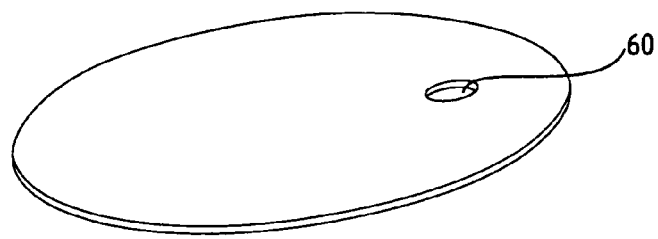
FIG. 3d is an enlarged perspective view of an adhesive layer according to an embodiment of the invention.

FIG. 3d illustrates the adhesive layer 20 in more detail. The adhesive layer 20 is made of a flexible material that is strong enough to hold the flexible mounting base in place. The adhesive layer 20 anchors the flexible sensor set at the infusion site to provide stability for the sensor set in a convenient and comfortable manner. In certain embodiments, the adhesive layer 20 includes an anti-bacterial agent to reduce the chance of infection; however, alternative embodiments may omit the agent. In further alternative embodiments, the mounting base may be other shapes, such as circular, oval, hour-glass, butterfly or the like. In addition, the adhesive layer may include an opening 60 through which the needle passes through before puncturing the patient's skin. The opening 60 frames the infusion site to guide the needle tip to the correct site.

Figure 4:
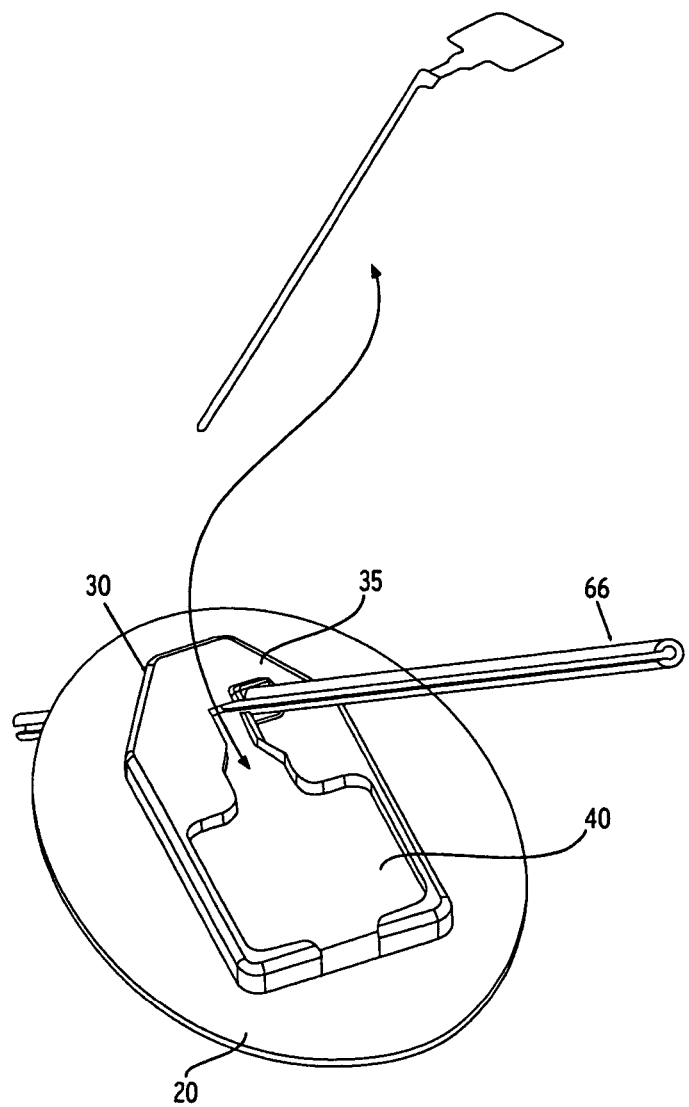
FIG. 4 is a partial flexible mounting base and a sensor according to an embodiment of the invention.

A partial flexible mounting base is shown in FIG. 4 with the outer flexible layer removed. As illustrated, a guide shaft 66 may be received into the needle insertion area 35 to stabilize the needle and substantially ensures safe, stable entry and exit for the needle at the infusion site. Also shown is a sensor 70 which fits into the flexible interface 40 of the semi-rigid housing 30.

Figure 5A:
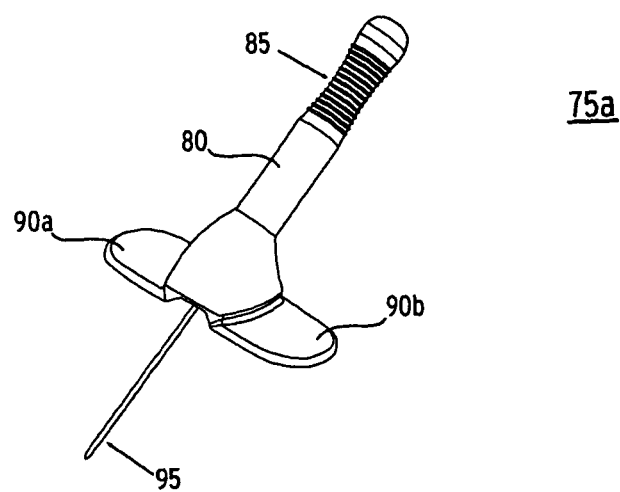
FIG. 5a is a perspective view of a safety needle that can be used with a flexible mounting base according to an embodiment of the invention.
Figure 5A:
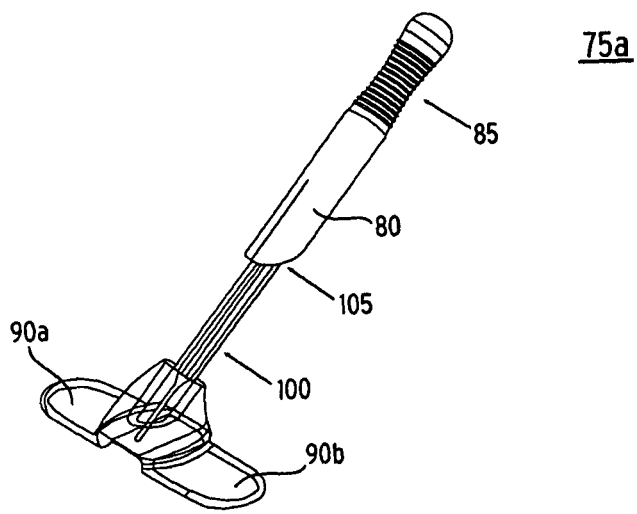
Figure 5B:
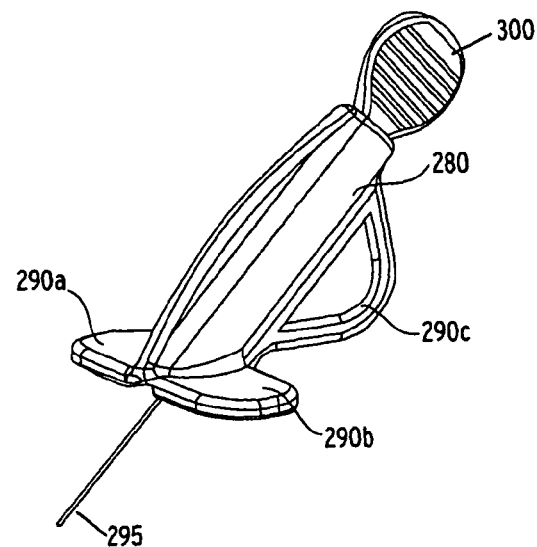
FIG. 5b is a perspective view of a safety needle that can be used with a flexible mounting base according to another embodiment of the invention.
Figure 5B:
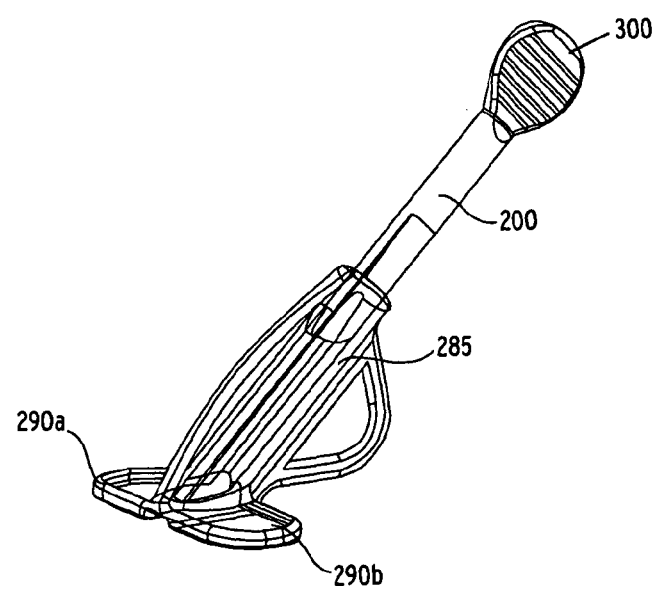

In further embodiments, a needle protection guard is included. When the insertion needle is withdrawn, a protective sheath (not shown) contained in the flexible mounting base is dislodged and covers the needle tip as the needle is separated from the flexible mounting base. In an alternative, the flexible mounting base may be used with a safety needle that has a handle covering one end of the needle to provide easier gripping. In FIGS. 5a and 5b, two different embodiments of a safety needle 75a, 75b are shown. The safety needle 75a of FIG. 5a has a handle 80 that is easy for a user to grip. There may be ridges 85 included to facilitate better ease of grip. In the embodiment shown, the safety needle 75a has wings 90a, 90b that are used to hold the safety needle 75a stable after the needle tip 95 is inserted subcutaneously through an infusion site. While holding the wings 90a, 90b, the user can grab the handle 80 and remove the safety needle 75a from the infusion site. As the needle tip 95 is pulled from the infusion site, a needle guide shaft 100 is extended to cover the needle tip 95 for safe disposal. A lock 105 may also be included to secure the guide shaft in place over the needle tip 95.

In an alternative configuration, the safety needle 75b of FIG. 5b has a handle 280 which includes two wings 290a, 290b that are used to hold the safety needle 75b stable after the needle tip 295 is inserted subcutaneously through an infusion site. A third wing 290c extends out from the handle 280 that provides an additional place for the user to hold the safety needle 75b in place prior to removal. A needle guide shaft 200 includes an end structure 300 that provides a manner of retracting the needle tip 295. The user pulls the end structure 300 and the safety needle 75b out from the infusion site while holding the insertion tool in place with either the two wings 290a, 290b or with the third wing 290c. The needle tip 295 and safety needle 75b is thus retracted into the handle 280 and a lock 205 secures the needle tip 295 in a covered position for safe disposal.

Figure 6:
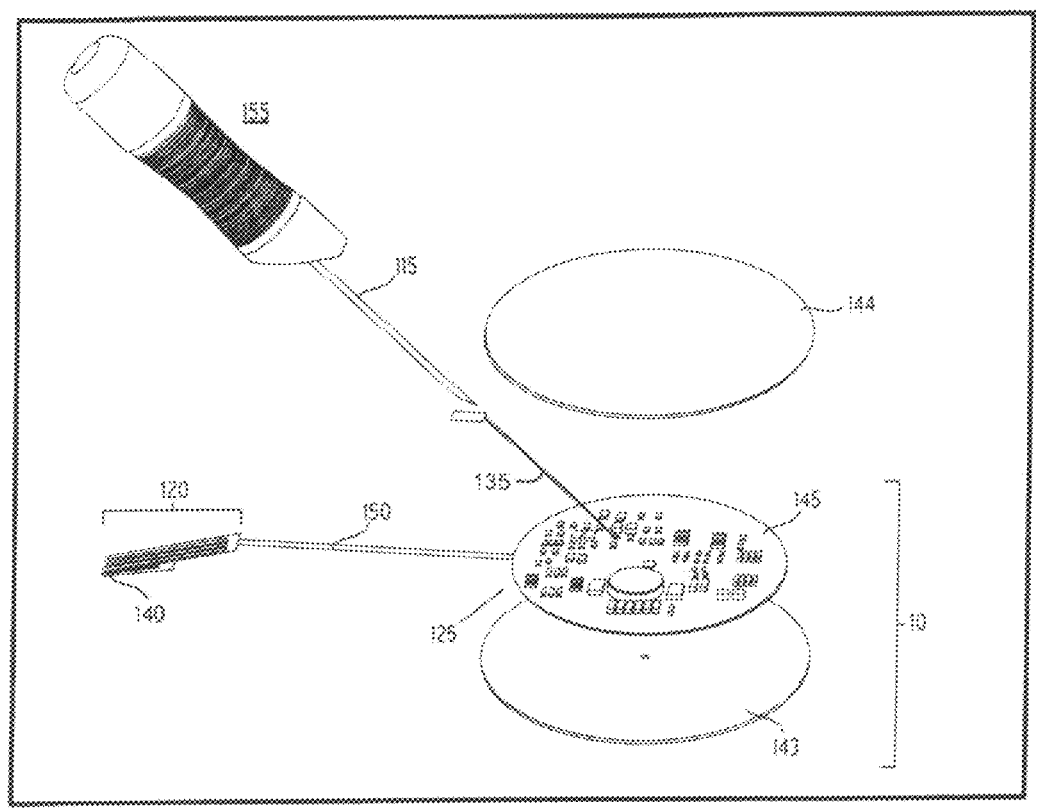
FIG. 6 is an exploded view of a flexible sensor with flexible electronics according to an embodiment of the invention.

In certain embodiments, a subcutaneous insertion set is provided with the flexible mounting base for placing the sensor at a selected site within the body of a patient. As shown in FIG. 6, the insertion set 155 comprises an insertion needle 115. The insertion needle 115 is adapted to extend through the partially shown flexible mounting base 10 adapted for seated mounting onto the patient's skin. The sensor 135 is connected to a flexible partial circuit 145, which is included in the flexible mounting base 10. The flexible partial circuit 145 is placed on an adhesive layer 143 and covered with a top layer 144. In FIG. 6, the flexible mounting base 10 is shown in an expanded configuration. The flexible partial circuit 145 is also connected to an extension lead 150 that leads to connector interface 120, which is adapted to be coupled to another electronic assembly to allow transfer of data to that electronic assembly. The sensor 135 may have one or more sensor electrodes thereon. Because the sensor interfaces directly with the electronics in this configuration, at least the basic electronics can be on the flexible partial circuit, as opposed to in a separate electronic assembly. For example, all of the circuitry that reads sensor information, digitizes the information, filters the data, calculates glucose, transmits information to the display, stores information, and so forth may be housed on the flexible circuit with or without a battery on board to power the sensor. Alternatively, minimal circuitry, such as the circuitry that reads the sensor information and digitizes the information could be included. The digitized information could be sent to another electronics assembly, which is electrically connected to the flexible circuit, with the remaining circuitry, including a transmitter and even a battery if desired to power the sensor from the other electronics assembly. Any desired distribution of circuitry between the minimal circuitry on the flexible circuit and full circuitry on the flexible circuit could be used, including a case in which duplicate circuitry is included both on the flexible circuit and the other electronics assembly.

When the flexible mounting base 10 is pressed onto the patient's skin, the insertion needle 115 pierces the skin to transcutaneously place the sensor 135. The insertion needle 115 can be withdrawn from the flexible mounting base 10, leaving the sensor 135 within the patient, to directly contact the patient fluid at the selected position within the patient, such as a subcutaneous, intravascular, intramuscular, or intravenous site. In further embodiments, a cannula (not shown) surrounds the sensor 135. When a cannula is used, the insertion needle 115 may be hollow so that at least a portion of the cannula is nested therein, with the insertion needle 115 defining a longitudinally extending slot along one side thereof to permit sliding withdrawal of the needle 115 from the flexible mounting base 10 and the nested portion of the cannula. Conductive contacts 140 on the connector interface 120 can be electrically connected to a suitable monitor device (not shown), either by wired or wireless communication, so that appropriate blood chemistry readings can be taken. Examples of wireless connection include, but are not limited to, RF, IR, WiFi, ZigBee and Bluetooth. Additional wireless connections further include single frequency communication, spread spectrum communication, adaptive frequency selection and frequency hopping communication. In the illustrated embodiment, the flexible partial circuit/sensor electronics 145 is shown as a layer in the flexible mounting base 10. However, in other embodiments, not shown, the sensor electronics may be contained in a housing separate from the flexible mounting base. In such an embodiment, a cable may be used to electrically couple the sensor to the separated sensor electronics to allow communication between the two. The sensor electronics 145 initially processes the analog current information to change it to digital data. In further embodiments, the sensor and the separated sensor electronics may use wireless communication, such as RF, IR, WiFi, ZigBee and Bluetooth.

If a cannula is used, during insertion, the insertion needle 115 and the protective cannula cooperatively protect and guide the sensor 135 to the desired transcutaneous placement position. The insertion needle 115 can then be withdrawn, whereupon slotted needle geometry permits the insertion needle 115 to slide over and longitudinally separate from the second portion of the cannula, thereby leaving the cannula and sensor 135 therein at the selected infusion site. In other embodiments, however, the flexible sensor may function without the use of a cannula.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are, therefore, to be considered in all respects as illustrative and not restrictive, the scope of the invention being indicated by the appended claims rather than the foregoing description. All changes that come within the meaning of and range of equivalency of the claims are intended to be embraced therein.

What is claimed is:

1. A sensor apparatus comprising:
   a flexible analyte sensor; and
   a flexible mounting base to carry the flexible analyte sensor including:
      a flexible adhesive layer to removably attach to a skin surface;
      a housing disposed on the adhesive layer to receive the flexible analyte sensor, said housing including a base layer and a plurality of sidewalls depending from said base layer; and
      a one-piece outer flexible layer that is entirely separate from the housing and from the flexible adhesive layer, wherein, once assembled, the flexible adhesive layer and the outer flexible layer enclose therebetween the entirety of the housing, including said plurality of sidewalls.

2. The sensor apparatus of claim 1, wherein the adhesive layer includes an opening for needle entry.

3. The sensor apparatus of claim 1, wherein the housing includes:
   a depression in said base layer adapted to receive the flexible analyte sensor; and
   a first opening in the base layer for needle entry.

4. The sensor apparatus of claim 3, wherein the housing further includes a second opening in the base layer to provide a path for a cable coupling the flexible analyte sensor to an external device.

5. The sensor apparatus of claim 4, wherein the first opening is located in one end of the base layer and the second opening is located on an opposing end of the base layer.

6. The sensor apparatus of claim 1, wherein the housing is flexible.

7. The sensor apparatus of claim 1, wherein the housing is semi-rigid.

8. The sensor apparatus of claim 1, wherein the housing comprises medical grade nylon.

9. The sensor apparatus of claim 1, wherein the flexible mounting base further includes a sealing layer disposed between the housing and the outer flexible layer.

10. The sensor apparatus of claim 9, wherein the sealing layer includes an area for needle entry.

11. The sensor apparatus of claim 10, wherein the sealing layer includes an opening to provide a path for a cable coupling the flexible analyte sensor to an external device.

12. The sensor apparatus of claim 11, wherein the area for needle entry is located in one end of the sealing layer and the opening is located on an opposing end of the sealing layer.

13. The sensor apparatus of claim 1, wherein the sealing layer comprises silicone.

14. The sensor apparatus of claim 1, wherein the sealing layer comprises a material selected from the group consisting of silicone, rubber latex, neoprene, nitrile, butyl, and vitron.

15. The sensor apparatus of claim 1, wherein the outer flexible layer includes an area for needle entry.

16. The sensor apparatus of claim 15, wherein the outer flexible layer further includes an opening to provide a path for a cable coupling the flexible analyte sensor to an external device.

17. The sensor apparatus of claim 16, wherein the area for needle entry is located in one end of the outer flexible layer and the opening is located on an opposing end of the outer flexible layer.

18. The sensor apparatus of claim 1, wherein the outer flexible layer includes a needle guide for needle entry.

19. The sensor apparatus of claim 1, wherein the outer flexible layer comprises cloth.

20. The sensor apparatus of claim 1, wherein the outer flexible layer comprises a material selected from the group consisting of polyurethane, polyethylene, polyester, polypropylene, and PTFE.

21. The sensor apparatus of claim 1, wherein the flexible analyte sensor is a thin film sensor.

22. The sensor apparatus of claim 1, wherein the flexible analyte sensor is an electrochemical sensor.

23. The sensor apparatus of claim 1, wherein the flexible analyte sensor is a glucose sensor.

24. The sensor apparatus of claim 1, wherein the flexible analyte sensor includes a proximal segment carried by the flexible mounting base, and a distal segment protruding from the flexible mounting base.

25. The sensor apparatus of claim 24, wherein the sensor proximal segment is connected to an external device through wired communication.

26. The sensor apparatus of claim 24, wherein the sensor proximal segment is connected to an external device through wireless communication.

27. The sensor apparatus of claim 26, wherein the wireless communication is selected from the group consisting of radio frequency and infrared.

28. The sensor apparatus of claim 24 further including a cannula protruding from the flexible mounting base, wherein at least a portion of the flexible analyte sensor is within the cannula.

29. The sensor apparatus of claim 28 further including a hollow insertion needle carried by the flexible mounting base to protrude therefrom and having at least a portion of the cannula nested therein, the insertion needle defining a longitudinally extending slot along one side thereof to permit sliding withdrawal of the needle from the flexible mounting base and the nested portion of the cannula.

30. The sensor apparatus of claim 29, wherein the insertion needle extends through the flexible mounting base, the insertion needle being manually withdrawable from the flexible mounting base for separation from the nested portion of the cannula.

31. The sensor apparatus of claim 29, wherein the needle further comprises a handle covering one end of the needle with a guide shaft contained therein.

32. The sensor apparatus of claim 31, wherein the handle further includes a lock to secure the guide shaft in a selected position.

33. The sensor apparatus of claim 32, wherein the selected position covers the entire needle.

34. The sensor apparatus of claim 1, wherein, once assembled, the outer flexible layer is in direct contact with the flexible adhesive layer about the entire periphery of the housing.

35. A sensor apparatus comprising:
   a flexible analyte sensor; and
   a flexible mounting base to carry the flexible analyte sensor including:
      a flexible adhesive layer to removably attach to a skin surface;
      a housing disposed on the adhesive layer to receive the flexible analyte sensor;

a sealing layer; and a one-piece outer flexible layer that is entirely separate from the housing and from the flexible adhesive layer, wherein the sealing layer is disposed atop the housing and beneath the outer flexible layer, wherein the sealing layer fully covers the housing, and wherein the flexible adhesive layer and the outer flexible layer enclose therebetween the entirety of the housing and the entirety of the sealing layer.

36. The sensor apparatus of claim 35, wherein the housing includes a base layer and a plurality of sidewalls depending from said base layer.

37. The sensor apparatus of claim 36, wherein the sealing layer includes a multiplicity of sidewalls, and wherein the sealing layer's side walls are in physical contact with, and cover, said sidewalls of the housing.

38. The sensor apparatus of claim 35, wherein the outer flexible layer includes an area for needle entry through an upper surface thereof.

* * * * *